United States Patent [19]

Prescott

[11] Patent Number: 6,107,246
[45] Date of Patent: Aug. 22, 2000

[54] HERBICIDAL FORMULATION AND METHOD OF CONTROLLING PLANTS

[75] Inventor: Grahame Prescott, Mooloolaba, Australia

[73] Assignee: Pizzeys, Brisbane, Australia

[21] Appl. No.: 09/194,472

[22] PCT Filed: May 30, 1997

[86] PCT No.: PCT/AU97/00343

§ 371 Date: Sep. 1, 1999

§ 102(e) Date: Sep. 1, 1999

[87] PCT Pub. No.: WO97/46102

PCT Pub. Date: Dec. 11, 1997

[30] Foreign Application Priority Data

May 30, 1996 [AU] Australia ................................. PO0165

[51] Int. Cl.[7] ............................ A01N 25/30; A01N 59/08
[52] U.S. Cl. ........................................... 504/116; 504/364
[58] Field of Search ...................................... 504/116, 364

[56] References Cited

U.S. PATENT DOCUMENTS

| | | | |
|---|---|---|---|
| 3,869,277 | 3/1975 | Berger et al. | 71/113 |
| 3,912,490 | 10/1975 | Boghosian | 71/28 |
| 4,162,155 | 7/1979 | Young | 71/110 |
| 5,168,655 | 12/1992 | Davidson et al. | 47/62 |
| 5,679,620 | 10/1997 | Magin et al. | 504/206 |
| 5,958,104 | 9/1999 | Nonomura et al. | 504/118 |

OTHER PUBLICATIONS

Van Keer et al. "Weed problems in a transitional upland rice based swidden system in northern Thailand" Highland Farming: Soil and the Future? Proceedings, Chiangmai, Thailand, Dec. 1995.

*Primary Examiner*—S. Mark Clardy
*Attorney, Agent, or Firm*—McDonnell Boehnen Hulbert & Berghoff; Steven J. Sarussi

[57] ABSTRACT

A herbicidal formulation comprising a salt, such as a metal halide; a microbiological food, such as a carbohydrate; a detergent and an oxidant, such as hydrogen peroxide, all mixed into a solution with a diluent. The herbicide provides a method of controlling plants by applying to a target plant the formulation which then dessicates the plant and selectively promotes the growth of pathogens whereby the target plant is overcome and perishes.

10 Claims, No Drawings

HERBICIDAL FORMULATION AND METHOD OF CONTROLLING PLANTS

This invention relates to a herbicidal formulation and method of controlling plants.

This invention has particular but not exclusive application to an environmentally friendly herbicide, and for illustrative purposes reference will be made to such application. However, it is to be understood that this invention could be used in other applications, using components which are selected on criteria other than environmental sensitivity, such as broad efficacy, appealing colour or odour or such like.

Herbicidal formulations presently base their efficacy on systemic invasion of a plant, causing disruption of the plant's biological function leading to plant death and subsequent decomposition. Herbicides almost always leave an undesirable residual in the soil which is ingested into surviving flora and fauna, leading to undesirable health and safety effects. Additionally, synthetic formulations frequently contain intractable poisons and toxins which accumulate, such as polychlorinated biphenols present in minute quantities in popular defoliants such as 24D and 245T, otherwise known as agent orange. Traditional herbicides are not formulated from natural materials or at least include an active ingredient of synthetic origin, and such synthetic materials are often associated with allergies, hypersensitivities and poor health.

Moreover, traditional herbicides are not intrinsically safe. The manufacturers of such formulations will go no further than to say that traditional herbicides are not known to cause harm, a statement which falls short of saying that such herbicides are harmless.

The present invention aims to alleviate one or more of the above disadvantages and to provide a herbicidal formulation and method of controlling plants which will be reliable and efficient in use. This invention also aims to provide a herbicidal formulation and method of controlling plants which is non-systemic, biodegradable and environmentally friendly With the foregoing in view, this invention in one aspect resides broadly in a herbicidal formulation including:

a salt;

a microbiological food;

a detergent, and an oxidant mixed into a solution with a diluent.

Preferably the salt is a metal halide, such as sodium chloride in aqueous solution in the range of from 125 g/L to saturation. In a preferred embodiment, the salt is sea salt in the range of from 200 g/L to 300 g/L, and more preferably, 250 g/L. it will be appreciated that the concentration of the salt may be determined by a consideration of the cost of same which decreases with concentration in balance with the efficacy of the mixture which increases with concentration.

Suitably, the microbiological food is a carbohydrate such as a sugar. The sugar may be any sugar or mixture of sugars, such as the sugar known by the trade name aspartame but preferably is a mono- or disaccharide or closely related thereto, and more preferably in the form of a sugar syrup such as molasses, treacle or such like. The sugar is preferably in the range of from 15 g/L to 25 g/L in the mixture.

The detergent may be any detergent known in the art for use in herbicidal formulations having the purpose, for example, of causing the formulation to stick to the surface of the target plant, and for some plant species, to break down the waxy coating on the exterior walls of the target plant. The preferred embodiment includes an alpha olefin sulfonate having a chain length in the range of from 12 to 14, however, it is to be appreciated that preferred detergents are completely biodegradable and environmentally friendly. Other detergents may be used such as d-limonene or materials containing same, such as for example the cleanser known by the trade mark ORANGE SQUIRT sold by Citrus Resources Australia.

The oxidant is also preferably environmentally friendly, such as hydrogen peroxide or such like, and preferably does not adversely affect the other components of the herbicidal formulation. Other oxidising agents may be used such as alkali perinanganates, perchlorates, dichromates and such like.

It will also be appreciated that additives may be substituted for one or more of the above preferred components if such additives include the preferred components so substituted. For example, chamomile herbal organic concentrate may be substituted for the alpha olefin sulfonate because it is known to contain alpha olefin sulfonate.

In a further aspect, this invention resides in a method of controlling plants by applying to a target plant a formulation which desiccates the target plant and selectively promotes the growth of pathogens whereby the target plant is overcome and perishes. Suitably, the formulation is non-systemic and includes a herbicidal formulation as hereinbefore defined.

In another aspect, this invention resides in a herbicidal formulation having a salt, sugar and oxidant concentration in solution sufficient to desiccate a target plant and a wetting agent having a concentration sufficient to permit the formulation to wet the surface of the target plant whereby the solution upon drying is substantially evenly distributed over the target plant. It is preferred that the sugar is in sufficient concentration to provide a food and/or energy source for naturally occurring plant pathogens to attack the desiccated target plant whereby the target plant is overcome thereby and dies.

If desired, pathogenic elements may be introduced or included in the formulation, and the formulation may be biologically active. Alternatively, a non-aqueous diluent may be used, such as alcohol, acetone or such like, to increase the drying rate of the formulation upon the target plant, however, it will be appreciated that the diluent chosen should be a solvent for sugar.

In order that this invention may be more readily understood and put into practical effect, reference will now be made to the following examples which illustrate a typical embodiment of the invention.

EXAMPLE 1

An aqueous solution comprising 250 g/L sea salt, 25 ml/L cane sugar molasses, 10 ml/L alpha olefin sulfonate and 10 g/L potassium pezmanganate was made and applied to plants of the species listed in the accompanying table. After application of the herbicidal formulation in accordance with this invention, all of the following plants displayed indicative symptoms associated with the retardation of plant vigour and a high order of pathogenic control following experimental field trials:

| Family | Common Name | Botanical Name |
|---|---|---|
| ASCLEPIADACEAE | Cotton Bush | Gomphcarpus spp |
| ASTERACEAE | Billy Goat Weed | Ageratum houstonianum |

-continued

| Family | Common Name | Botanical Name |
|---|---|---|
| | Bindii | *Soliva pterosperma* |
| | Cobblers Pegs | *Bidens pilosa* |
| | Fireweed | *Senecio spp* |
| | Flatweed | *Hypochoeris radicata* |
| | Groundsel | *Baccharis halimifolia* |
| | Japanese Sunflower | *Tithonia diversifolia* |
| | Milk Thistle | *Sonchus oleraceus* |
| | Mist Flower | *Ageratina riparia* |
| | Potato Weed | *Galinsoga parviflora* |
| | Stinking Roger | *Tagetes minuta* |
| CONVULVACEAE | Kidney Weed | *Dichondra repens* |
| CYPERACEAE | Mullimbimby Couch | *Cyperus brevifolius* |
| FABACEAE | Clover | *Trifolium subteeraneum* |
| | Legume | *Macroptilium lathyroides* |
| | Phasey Bean | *Macroptilium lathyroides* |
| | Rattle Pod | *Crotalaria sp* |
| POACEAE | Blady Grass | *Imperata cylindrica* |
| | Carpet Grass | *Axonopus spp* |
| | Kikuyu | *Pennisetum clandestinum* |
| | Paspalum | *Paspalum dilitatum* |
| SOLONACEAE | Wild Tobacco | *Solanum sp* |
| VERBENACEAE | Lantana | *Lantana camara* |

The herbicidal formulation of the present invention may be placed into back mounted tanks or smaller hand pump spray appliances. The dry ingredients are added to the tank and the sea salt added thereto in the required quantities, whereupon water is added and stirred until the solids are completely dissolved. After the solution is complete, the detergent is added and stirred, and the final quantity of water added to make the formulation the required strength.

The herbicidal formulation so produced is sprayed liberally on target plants until a good coverage is achieved, using a standard nozzle adjusted to a fine mist.

It will of course be realised that while the above has been given by way of illustrative example of this invention, all such and other modifications and variations thereto as would be apparent to persons skilled in the art are deemed to fall within the broad scope and ambit of this invention as claimed in the following claims.

What is claimed is:

1. A herbicidal formulation including:

a salt;

a microbiological food;

a detergent, and an oxidant mixed into a solution with a diluent.

2. A herbicidal formulation as claimed in claim 1, wherein the salt is mixed in an aqueous solution in the range of from 125 g/L to saturation and the microbiological food is a sugar mixed in the aqueous solution in the range of from 15 g/L to 25 g/L.

3. A herbicidal formulation as claimed in claim 1, wherein the salt is sea salt in the range of from 200 g/L to 300 g/L.

4. A herbicidal formulation as claimed in claim 2, wherein the sugar is in the form of a sugar syrup selected from molasses and treacle.

5. A herbicidal formulation as claimed in claim 1, wherein the detergent is alpha olefin sulfonate having a chain length in the range of from 12 to 14.

6. A herbicidal formulation as claimed in claim 1, wherein the oxidant is selected from non-halogen soluble oxidizing agents which do not adversely affect the other components of the herbicidal formulation.

7. A herbicidal formulation as claimed in claim 6, wherein the soluble oxidizing agent is hydrogen peroxide.

8. A herbicidal formulation as claimed in claim 1, wherein the detergent is contained in chamomile herbal organic concentrate.

9. A method of controlling plants by applying to a target plant a formulation which desiccates the target plant and selectively promotes the growth of pathogens whereby the target plant is overcome and perishes.

10. A method as claimed in claim 9, wherein the formulation is non-systemic and includes a herbicidal formulation as claimed in claim 1.

* * * * *